US008815534B2

United States Patent
Foussat et al.

(10) Patent No.: US 8,815,534 B2
(45) Date of Patent: Aug. 26, 2014

(54) METHOD FOR ASSESSING THE EFFICACY OF A TR1 CELL THERAPY IN A SUBJECT

(75) Inventors: Arnaud Foussat, Biot (FR); Brigitte Quatannens, Mandelieu-la-Napoule (FR)

(73) Assignee: TxCell, Valbonne (FR)

( * ) Notice: Subject to any disclaimer, the term of this patent is extended or adjusted under 35 U.S.C. 154(b) by 0 days.

(21) Appl. No.: 13/878,089

(22) PCT Filed: Oct. 7, 2011

(86) PCT No.: PCT/IB2011/002680
§ 371 (c)(1),
(2), (4) Date: Apr. 5, 2013

(87) PCT Pub. No.: WO2012/046139
PCT Pub. Date: Apr. 12, 2012

(65) Prior Publication Data
US 2013/0224784 A1    Aug. 29, 2013

Related U.S. Application Data

(60) Provisional application No. 61/391,133, filed on Oct. 8, 2010.

(30) Foreign Application Priority Data

Oct. 8, 2010    (EP) .................................... 10368038

(51) Int. Cl.
| C12Q 1/02 | (2006.01) |
| C12N 5/00 | (2006.01) |
| C12N 5/071 | (2010.01) |

(52) U.S. Cl.
USPC ............................. 435/29; 435/325; 435/372

(58) Field of Classification Search
USPC ............................................ 435/29, 325, 372
See application file for complete search history.

(56) References Cited

U.S. PATENT DOCUMENTS

8,035,084 B2    10/2011    Sumi
2008/0233095 A1    9/2008    Groux et al.

FOREIGN PATENT DOCUMENTS

| WO | 2006/018674 A1 | 2/2006 |
| WO | 2009/054242 A1 | 4/2009 |
| WO | 2009/068575 A1 | 6/2009 |

OTHER PUBLICATIONS

Von Baehr et al. Improving the In Vitro Antigen Specific T Cell Proliferation Assay: The Use of Interferon-Alpha to Elicit Antigen Specific Stimulation and Decrease Bystander Proliferation; Journal of Immunological Methods, vol. 251, No. 1-2 (2001) pp. 63-71.*
Klein et al. In Vivo Dynamics of Antigen-Specific Regulatory T Cells Not Predicted From Behavior In Vitro; PNAS, vol. 100, No. 15 (2003) pp. 8886-8891.*
International Search Report, dated Jan. 27, 2012, from corresponding PCT application.
Francoise Cottrez et al., "T Regulatory Cells 1 Inhibit a Th2-Specific Response In Vivo", Journal of Immunology, Nov. 1, 2000, pp. 4848-4853, vol. 165, No. 9.

* cited by examiner

*Primary Examiner* — Susan Hanley
*Assistant Examiner* — Paul Martin
(74) *Attorney, Agent, or Firm* — Young & Thompson (57) ABSTRACT

A method for assessing whether a patient subjected to an antigen-specific Tr1 cell therapy is responding to the treatment, includes: determining in vitro the antigen-specific proliferation of T cells contained in a cell sample from the patient; and comparing the antigen-specific proliferation to a standard reference, thereby determining whether the patient is responding or not to the treatment.

11 Claims, 5 Drawing Sheets

METHOD FOR ASSESSING THE EFFICACY OF A TR1 CELL THERAPY IN A SUBJECT

FIELD OF THE INVENTION

The invention relates to a method for assessing the efficacy of a Tr1 cell therapy in a subject and thus determining whether a patient subjected to a Tr1 cell therapy is a responder or a non-responder to said therapy.

BACKGROUND OF THE INVENTION

Treatment of a disease or a condition with a biologic compound presents a number of challenges. One of them is to determine which patient population is eligible for a particular treatment, which subjects are going to respond to this treatment and which subjects will lose response after a certain amount of time. This information has significant impacts upon further patient's care and clinical study designs.

Biomarkers are usually helping for answering these questions.

A biomarker may be defined as "a characteristic that is objectively measured and evaluated as an indicator of normal biological processes, pathogenic processes or pharmacologic responses to a therapeutic intervention".

In the art, a great number of studies describe the use of molecules such as cytokines or the use of gene expression profiles to determine whether or not the treated subject is going to be a responder to the treatment.

For example, molecules such as CRP and cytokines such as IL-1 beta, IL-2, IL-6, IL-8, IL-12 or interferon gamma have been described as biomarkers to define the response of subjects with Crohn's disease to infliximab and other biologic compounds. WO2008/147869 describes the determination of at least one gene expression among IP-10, MCP-1, MMP-9, TNF alpha, EGF, IL-6, ENA-78, MPO, MIP-1 beta and VEGF for evaluating the efficacy of a treatment for gastrointestinal disorders. WO2008/048986 also relies on measuring expression of genes selected in a list for classifying individuals as responder or non-responder to a treatment for inflammatory bowel diseases. Another example is EP2056110 describing the detection of specific proteins to assess the responsiveness to an anti-TNF treatment.

The present invention relates to Tr1 cell therapy used for treating chronic inflammatory diseases, autoimmune diseases, allergic diseases, and organ transplantation conditions. As shown previously, Tr1 cells can be used for treating multiple sclerosis (WO2009052283), intestinal inflammatory conditions such as Crohn's disease (WO2009068575) or arthritic conditions such as rheumatoid arthritis (WO2009054242).

Although biomarkers have been described for evaluating the outcome of therapies against those conditions, there is a need for biomarkers that will specifically allow the prediction of the outcome of a Tr1 cell therapy. There is a need for stratification of patients who are being subjected to a Tr1 cell therapy and for distinguishing between Tr1 cell therapy responder and non responder patients.

SUMMARY

One object of the invention is a method for assessing whether a patient, preferably a human patient, subjected to an antigen-specific Tr1 cell therapy is responding to the treatment, said method comprising:
   determining in vitro the antigen-specific proliferation of T cells contained in a cell sample from said patient,
   comparing said antigen-specific proliferation to a standard reference,
thereby determining whether the patient is responding or not to the treatment.

In one embodiment of the invention, the standard reference is a standard reference obtained from the patient, which is the antigen-specific proliferation of T cells contained in a cell sample obtained from said patient before Tr1 cell treatment.

In another embodiment of the invention, the cell sample containing T cells is obtained from the patient between day 5 and day 30 after the last administration of Tr1 cells to the patient. In one embodiment, the in vitro determination of the antigen-specific proliferation of T cells is carried out in a cell sample obtained from the patient between day 5 and day 30 after the last administration of Tr1 cells to the patient.

In another embodiment of the invention, the cell sample is peripheral blood mononuclear cells, peripheral white blood cells or is obtained from a lymph nodes biopsy, an intestinal biopsy, a synovial biopsy, a cerebrospinal fluid or from a bronchoalveolar lavage.

In another embodiment of the invention, the assessment of the antigen-specific proliferation of T cells comprises:
   culturing the cell sample containing T cells in the presence of the antigen to which the Tr1 cells are directed, and
   determining the proliferation of T cells after 2 to 10 days of culture.

In another embodiment of the invention, the method as described here above is repeated each week on a cell sample obtained from the patient each week during day 5 to day 30 after the last administration of Tr1 cells to the patient.

In another embodiment of the invention, the method as described here above is repeated every two weeks on a cell sample obtained from the patient every two weeks during day 5 to day 30 after the last administration of Tr1 cells to the patient.

Another object of the invention is the method as described here above for sorting the patient into responder or non-responder group.

Another object of the invention is the method as described here above for monitoring disease progression and monitoring the therapeutic outcome.

Another object of the invention is the method as described here above for assessing whether a patient having a Crohn's disease and subjected to an ovalbumin-specific Tr1 cell therapy is responding to the treatment.

Another object of the invention is the method as described here above for assessing whether a patient having a rheumatoid arthritis and subjected to a type II collagen-specific Tr1 cell therapy is responding to the treatment.

Another object of the invention is the method as described here above for assessing whether a patient subjected to an antigen-specific Tr1 cell therapy is responding to the treatment. Advantageously, said method is for assessing in vitro whether a patient subjected to an antigen-specific Tr1 cell therapy is responding to the treatment.

DETAILED DESCRIPTION OF THE INVENTION

Tr1 cell therapy as previously described by the inventors is based on administration of antigen-specific Tr1 cells to a subject. In one embodiment of the invention, the antigen-specific Tr1 cells are not stimulated with said antigen prior to administration. In one embodiment of the invention, the Tr1 cell therapy does not comprise the administration of the antigen to which the Tr1 cells are specific. The selection of the antigen is made according to the disease or condition to be treated. For example, for treating an intestinal inflammatory condition such as Crohn's disease, Tr1 cells specific for a food antigen from common human diet such as ovalbumin are used.

The inventors assessed the proliferation of T cells contained in a cell sample obtained from the treated patient in response to the antigen to which the Tr1 cells are specific. They made the observation that an inhibition of said proliferation correlates with the disease improvement and the clinical response of the patient.

One object of the invention is thus a method for assessing whether a patient subjected to an antigen-specific Tr1 cell therapy is responding to the treatment, said method comprising:

determining in vitro the antigen-specific proliferation of T cells contained in a cell sample from said patient, comparing said antigen-specific proliferation to a standard reference, thereby determining whether the patient is responding or not to the treatment.

In one embodiment, the patient is a human.

In one embodiment, the patient does not respond adequately to, or is unlikely to respond adequately to, one or more therapeutic agent selected in the group comprising anti-TNF, natalizumab, anti-interleukins such as, for example, anti-IL1, anti-IL6, anti-IL12, anti-IL17 and anti-IL23; anti-B lymphocytes; anti-costimulatory molecules; tolerogenic agents; anti-complement proteins; inhibitors of T cell signalling molecules; inhibitors of cell migration; IL-1 receptor antagonist analogs (anakinra); 5 aminosalicyclic acid and analogs such as mesalazine, sulfazaline, sulfasalazine, olsalazine, balsalazide; corticoids such as prednisone, budesonide, hydrocortisone, prednisolone, methylprednisolone, betamethasone, bedomethasone, tixocortol; probiotics such as saccharomyces boulardii; methotrexate; hydroxychloroquine; azathioprine; 6-mercaptopurine; cyclosporine; minocycline; D-penicillamine; thalidomide; leflunomide or leflumide.

As used herein, the expressions "inadequate response", "does not respond adequately to", or "unlikely to respond adequately" refer to an actual or probable response by a patient which indicates that the therapy has been, or is likely to be, ineffective, toxic, or poorly tolerated insofar as the patient is concerned.

The term "Tr1 cells" as used herein refers to cells having the following phenotype at rest $CD4^+CD25^-FoxP3^-$ and capable of secreting high levels of IL-10 and significant levels of TGF-β upon activation. Tr1 cells are characterized, in part, by their unique cytokine profile: they produce high levels of IL-10, significant levels of TGF-β and intermediate levels of IFN-γ, but little or no IL-4 or IL-2. The cytokine production is typically evaluated in cultures of cells after activation with polyclonal activators of T lymphocytes such as anti-CD3+ anti-CD28 antibodies or Interleukin-2, PMA+ionomycin. Alternatively, the cytokine production is evaluated in cultures of cells after activation with the specific T-cell antigen presented by antigen presenting cells. High levels of IL-10 correspond to at least about 500 pg/ml, typically greater than about 1, 2, 4, 6, 8, 10, 12, 14, 16, 18, or 20 thousand pg/ml or more. Significant levels of TGF-β correspond to at least about 100 pg/ml, typically greater than about 200, 300, 400, 600, 800, or 1000 pg/ml or more. Intermediate levels of IFN-γ correspond to concentrations comprised between 0 pg/ml and at least about 400 pg/ml, typically greater than about 600, 800, 1000, 1200, 1400, 1600, 1800, or 2000 pg/ml or more. Little or no IL-4 or IL-2 corresponds to less than about 500 pg/ml, preferably less than about 250, 100, 75, or 50 pg/ml, or less.

The term "treatment" as used herein refers to therapeutic treatment and prophylactic and preventative measures, wherein the object is to prevent or slow down (lessen, diminish) the targeted pathological disorder or condition. Tr1 treatment and Tr1 therapy are used herein with the same meaning.

The term "standard reference" as used herein broadly encompasses any suitable reference standard which may be used as a basis for comparison with respect to the measured variable. Preferably, the standard reference is a personalized reference, determined using a cell sample containing T cells obtained from the patient before Tr1 treatment.

In one embodiment of the invention, the standard reference is the proliferation of the T cells obtained from the patient before Tr1 treatment and measured in vitro. Accordingly, a cell sample containing T cells is obtained from the patient before Tr1 treatment; preferably on the day of the first Tr1 cells infusion before Tr1 cells injection, and proliferation of the T cells is assessed to determine the standard reference.

In one embodiment, the standard reference is an index value or is derived from one or more risk prediction algorithms or computed indices for the response to a Tr1 cell therapy. A standard reference can be relative to a number or value derived from population studies, including without limitation, such subjects having similar age range, subjects in the same or similar ethnic group, subjects having family histories of chronic inflammatory diseases, autoimmune diseases or allergic diseases; or relative to the starting sample of a subject undergoing Tr1 cell therapy, for a chronic inflammatory disease, an autoimmune disease or an allergic disease.

In one embodiment, the standard reference is constructed using algorithms and other methods of statistical and structural classification.

In one embodiment of the invention, the standard reference is derived from the measurement of the proliferation of T cells in response to the antigen to which the Tr1 cells are specific in a control sample derived from one or more subjects who are substantially healthy. As used herein, a "substantially healthy subject" has not been previously diagnosed or identified as having or suffering from a chronic inflammatory disease, an autoimmune disease or an allergic disease.

In another embodiment of the invention, the standard reference is derived from the measurement of the proliferation of T cells in response to the antigen to which the Tr1 cells are specific in a control sample derived from one or more subjects who are diagnosed or identified as having or suffering from a chronic inflammatory disease, an autoimmune disease or an allergic disease.

In another embodiment of the invention, the standard reference is derived from the measurement of the proliferation of T cells in response to the antigen to which the Tr1 cells are specific in a sample derived from one or more subject who has been previously identified as responder(s) to a Tr1 cell therapy for treating a chronic inflammatory disease, an autoimmune disease or an allergic disease.

In another embodiment of the invention, the standard reference is derived from the measurement of the proliferation of T cells in response to the antigen to which the Tr1 cells are specific in a sample derived from one or more subject who has been previously identified as non-responder(s) to a Tr1 cell therapy for treating a chronic inflammatory disease, an autoimmune disease or an allergic disease.

According to one embodiment of the invention, the cell sample comprises T cells and antigen presenting cells.

Cell samples obtainable from the patient and containing T cells and antigen presenting cells include, but are not limited to, peripheral blood mononuclear cells (PBMC), peripheral white blood cells, cell sample obtained from tissue biopsies such as lymph nodes biopsies, intestinal or synovial biopsies, cell sample obtained from bronchoalveolar lavage or a cerebrospinal fluid.

Methods for obtaining PBMC from the patient include, but are not limited to, leukapheresis or whole blood collection followed by PBMC purification using density gradient centrifugation (ficoll).

Methods for obtaining peripheral white blood cells or leukocytes include, but are not limited to, red cells filtration or lysis from blood sample.

One example of the method for assessing whether a patient subjected to an antigen-specific Tr1 cell therapy is responding to the treatment is the following:
 culturing the cell sample containing T cells obtained from the subject in the presence of the antigen to which the Tr1 cells are directed,
 determining the T cells proliferation.

In one embodiment of the invention, the cell sample containing T cells obtained from the subject is cultured in the presence of the antigen to which the Tr1 cells are directed and in the absence of said antigen.

The culture without said antigen is a negative control of basal T cells proliferation in the absence of activation.

In one embodiment of the invention, the cell sample containing T cells is cultured during 2 to 10 days, preferably during 3 to 6 days, more preferably during 5 days.

In one embodiment of the invention, the concentration of cells to be cultured is $10^4$ to $10^7$ cells/ml, preferably $10^5$ to $10^6$ cells/ml, more preferably $10^6$ cells/ml.

In one embodiment of the invention, the concentration of antigen is from 0.1 µg/ml to 10 mg/ml of antigen, preferably from 1 µg/ml to 1 mg/ml, more preferably is of about 1 mg/ml of antigen. As used herein, the term "about" preceding a figure means more or less 10% of the value of said figure.

In one embodiment of the invention, the cell sample containing T cells is cultured in a T cell medium supplemented with serum or in a serum free medium.

Examples of T cell serum-free medium include, but are not limited to, X-VIVO and AIM-V. Examples of T cell serum supplemented with serum include, but are not limited to, RPMI or ISCOVE medium preferably supplemented with human Serum AB or autologous plasma.

In one embodiment of the invention, the cell sample containing T cells is cultured at temperature from 35° C. to 39° C., preferably about 37° C., in an atmosphere of about 5% $CO_2$.

According to the invention, the proliferation of the T cells contained in a cell sample obtained from the patient in response to the specific antigen to which the Tr1 cells are directed is assessed by conventional methods known in the art.

Examples of said methods include, but are not limited to, tritiated thymidine assay, change in DNA content measurement, BrdU incorporation assay, viability markers measurement such as WST1 or MTT, Promega cell titer 96 AQueous non-radioactive cell proliferation assay or Promega CellTiter 96 Aqueous One Solution Cell Proliferation Assay Kit, and Flow cytometry assays using CFSE or PKH26.

In one embodiment of the invention, the cell sample containing T cells is obtained from the patient between day 5 and day 30 after the last administration of the antigen-specific Tr1 cells to the patient.

In one embodiment of the invention, the cell sample containing T cells is obtained from the patient between day 6 and day 30, between day 7 and day 30, between day 8 and day 30, between day 9 and day 30, between day 10 and day 30, between day 11 and day 30, between day 12 and day 30, between day 13 and day 30, between day 14 and day 30, between day 15 and day 30, between day 16 and day 30, between day 17 and day 30, between day 18 and day 30, between day 19 and day 30, between day 20 and day 30 or between day 21 and day 30 after the administration of the antigen-specific Tr1 cells to the patient.

In one embodiment, a method for assessing whether a patient subjected to an antigen-specific Tr1 cell therapy is responding to the treatment comprises the following steps:
 assessing the proliferation of T cells in a cell sample obtained from the patient before Tr1 treatment, preferably on the day of the first Tr1 cells infusion before Tr1 cells injection, said proliferation being the standard reference;
 carrying out the Tr1 cell therapy, comprising one or more Tr1 cells injections;
 assessing the proliferation of T cells in a cell sample obtained from the patient 5, 6, 7, 8, 9, 10, 11, 12, 13, 14, 15, 16, 17, 18, 19, 20, 21, 22, 23, 24, 25, 26, 27, 28, 29 or 30 days after the last injection of Tr1 cells; and
 comparing said T cell proliferation determined after the Tr1 cells injection to the standard reference.

In one embodiment, said T cell proliferation value or index is calculated as following: (T cell proliferation in the presence of the antigen to which the Tr1 cells are directed)/(T cell proliferation in the absence of the antigen to which the Tr1 cells are directed)

In one embodiment, a method for assessing whether a patient subjected to an antigen-specific Tr1 cell therapy is responding to the treatment comprises the following steps:
 carrying out the Tr1 cell treatment, comprising one or more Tr1 cells injections;
 assessing the proliferation of T cells in a cell sample obtained from the patient 5, 6, 7, 8, 9, 10, 11, 12, 13, 14, 15, 16, 17, 18, 19, 20, 21, 22, 23, 24, 25, 26, 27, 28, 29 or 30 days after the last injection of Tr1 cells; and
 comparing said T cell proliferation with a standard reference.

In one embodiment of the invention, a cell sample containing T cells is obtained from the patient before the Tr1 treatment and each week after the last administration of the Tr1 treatment, during at least 4 weeks. Accordingly, the method of the invention is performed each week.

In another embodiment of the invention, a cell sample containing T cells is obtained from the patient before the Tr1 treatment and every two weeks after the last administration of the Tr1 treatment, during at least 4 weeks. Accordingly, the method of the invention is performed every two weeks.

In another embodiment of the invention, a cell sample containing T cells is obtained from the patient before the Tr1 treatment and every 10 days after the last administration of the Tr1 treatment, during at least 4 weeks. Accordingly, the method of the invention is performed every 10 days.

In one embodiment of the invention, a cell sample containing T cells is obtained from the patient before the Tr1 cells administration and every week after the administration, during at least 8 weeks.

In one embodiment of the invention, a cell sample containing T cells is obtained from the patient before the Tr1 cells administration and every two weeks after the administration, during at least 8 weeks.

In one embodiment of the invention, a cell sample containing T cells is obtained from the patient before the Tr1 cells administration and every 4 weeks after the administration, during at least 8 weeks.

In one embodiment of the invention, a cell sample containing T cells is obtained from the patient before the Tr1 cells administration and every month after the administration, during at least 2 months.

In one embodiment of the invention, a cell sample containing T cells is obtained from the patient before the Tr1 cells administration and at week 3 and/or week 5 and/or at week 8 after the administration.

According to the invention, the decrease of the T cells proliferation compared to the standard reference indicates that the subject is responding to the treatment.

In one embodiment of the invention, a decrease of T cells proliferation in the presence of antigen superior or equal to 20% compared to the standard reference indicates that the subject is responding to the treatment.

In another embodiment of the invention, a decrease of T cells proliferation in the presence of antigen superior or equal to 30%, 40%, 50% compared to the standard reference indicates that the subject is responding to the treatment.

In another embodiment of the invention, a decrease of T cells proliferation in the presence of antigen superior or equal to 60%, 70%, 80%, 90% compared to the standard reference indicates that the subject is responding to the treatment.

In another embodiment of the invention, a proliferation index (PI) may be determined at each measurement:

$$PI = \text{T cells proliferation in the presence of antigen/T cells proliferation in the absence of antigen.}$$

A determined PI at a given time less than the standard reference PI indicates that the subject is responding to the treatment.

In another embodiment of the invention, a proliferation ratio (PR) may be determined:

$$PR = (PI)_t / (PI)_{t0}.$$

$(PI)_t$ represents the proliferation index determined at a given time, for example determined at 3 weeks or 8 weeks after Tr1 cell administration to the patient.

$(PI)_{t0}$ represents the proliferation index determined at t0 which is the proliferation index of the standard reference or which is the proliferation index calculated from the antigen specific proliferation of T cells in a cell sample obtained from the patient before the injection of Tr1 cells to said patient.

A PR less than 1 indicates that the subject is responding to the treatment.

One object of the invention is a method for assessing whether a patient subjected to an antigen-specific Tr1 cell therapy is responding to the treatment, said method comprising:
  determining the antigen-specific proliferation of T cells contained in a cell sample from said patient in vitro,
  comparing said antigen-specific proliferation to a standard reference,
thereby sorting the subject into responder or non-responder group.

The term "responder" as used herein refers to a patient that responds or is likely to respond in a near future to the therapy or treatment.

The term "non-responder" as used herein refers to a patient that does not respond or is unlikely to respond in a near future to the therapy or treatment.

Accordingly, classification of a patient as a "responder" indicates that Tr1 treatment is successful, while a patient identified as "non-responder" would likely try different therapies.

Classifying patients as responder or non-responder is advantageous as it allows the prediction of the optimal course of therapy for the patient.

In one embodiment, a patient having a PR less than 1 determined 2 weeks, preferably 3 weeks after Tr1 cells administration, has a chance greater than 50% of responding to that therapy.

Preferably, in the present invention, a patient having a PR less than 1 determined 2 weeks, preferably 3 weeks after Tr1 cells administration, has a chance greater than 60%, 70%, 80%, 90% or 95% or more of responding to the Tr1 cell therapy.

In one embodiment, a patient having a PR less than 1 determined from 3 weeks to 8 weeks after Tr1 cells administration, has a chance greater than 50% of responding to that therapy.

Preferably, in the present invention, a patient having a PR less than 1 determined from 3 weeks to 8 weeks after Tr1 cells administration, has a chance greater than 60%, 70%, 80%, 90% or 95% or more of responding to the Tr1 cell therapy.

According to the invention, assaying the proliferation of T cells obtained from the patient as described here above allows the monitoring of the disease and the monitoring of the therapeutic outcome.

According to the invention, assaying the proliferation of T cells obtained from the patient as described here above allows the evaluation of the patient's risk of not responding to the treatment and that his/her condition does not improve.

According to the invention, assaying the proliferation of T cells obtained from the patient as described here above allows the stratification or classification of a group of patients.

According to the invention, the above described method is for assessing whether a patient having an intestinal inflammatory condition and subjected to a Tr1 cell therapy is responding to the treatment. In said treatment, the patient is subjected to a Tr1 cell therapy, wherein the Tr1 cells are specific of a food antigen from the common human diet.

The term "food antigen from common human diet" refers to an immunogenic peptide, which comes from foodstuffs common for humans, such as food antigens of the following non-limiting list: bovine antigens such as lipocalin, Ca-binding S100, alpha-lactalbumin, lactoglobulins such as beta-lactoglobulin, bovine serum albumin, caseins. Food-antigens may also be atlantic salmon antigens such as parvalbumin, chicken antigens such as ovomucoid, ovalbumin, Ag22, con-albumin, lysozyme or chicken serum albumin, peanuts, shrimp antigens such as tropomyosin, wheat antigens such as agglutinin or gliadin, celery antigens such as celery profilin, carrot antigens such as carrot profilin, apple antigens such as thaumatin, apple lipid transfer protein, apple profilin, pear antigens such as pear profilin, isoflavone reductase, avocado antigens such as endochitinase, apricot antigens such as apricot lipid transfer protein, peach antigens such as peach lipid transfer protein or peach profilin, soybean antigens such as HPS, soybean profilin or (SAM22) PR-I0 prot, fragments, variants and mixtures thereof.

As used herein the term "fragment" of an antigen refers to any subset of an antigen, as a shorter peptide. In one embodiment, a fragment of an antigen is a peptide of at least 6 amino acids in length. In one embodiment, a fragment of an antigen is a peptide of 6 to 50 amino acids in length, preferably of 6 to 30 amino acids, more preferably of 6 to 20 amino acids in length.

The term "variant" of an antigen, such as, for example, a food antigen from common human diet, refers herein to an antigen that is almost identical to the natural antigen and which shares the same biological activity. The minimal difference between the natural antigen and its variants may lie for example in an amino-acid substitution, deletion, and/or addition. Such variants may contain for example conservative amino acid substitutions in which amino acid residues are replaced with amino acid residues having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In one embodiment, the variant of an antigen presents a sequence identity of at least or about 70, 75, 80, 85, 90, 91, 92, 93, 94, 95, 96, 97, 98, 99% with the sequence of the natural antigen. The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

The term "inflammatory intestinal condition" refers to inflammatory bowel disease, ulcerative colitis, Crohn's disease, intestinal inflammation linked to food allergy or intolerance, intestinal inflammation linked to milk protein allergy, intestinal inflammation linked to celiac disease, intestinal inflammation linked to hen egg allergy, or intestinal inflammation linked to peanut allergy.

According to the invention, the cell sample containing T cells obtained from the patient is cultured in the presence of the food antigen from common human diet to which the Tr1 cells infused in the patient are directed. After 2 to 10 days, the proliferation of the T cells is assessed and compared to the proliferation of the standard reference, for example the proliferation of T cells obtained from the patient before Tr1 treatment.

In one embodiment of the invention, the method of the invention is for assessing whether a patient having a Crohn's disease and subjected to an ovalbumin-specific Tr1 cell therapy is responding to the treatment.

According to the invention, the above described method is for assessing whether a patient having a multiple sclerosis condition and subjected to a Tr1 cell therapy is responding to the treatment. In said treatment, the patient is subjected to a Tr1 cell therapy, wherein the Tr1 cells are specific of a multiple sclerosis-associated antigen. The term "multiple sclerosis-associated antigen" refers to myelin basic protein (MBP), myelin associated glycoprotein (MAG), myelin oligodendrocyte protein (MOG), proteolipid protein (PLP), oligodendrocyte myelin oligoprotein (OMGP), myelin associated oligodendrocyte basic protein (MOBP), oligodendrocyte specific protein (OSP/Claudinl 1), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase), fragments, variants and mixtures thereof.

According to the invention, the cell sample containing T cells obtained from the patient is cultured in the presence of the multiple sclerosis-associated antigen to which the Tr1 cells infused in the patient are directed. After 2 to 10 days, the proliferation of the T cells is assessed and compared to the proliferation of the standard reference, for example the proliferation of T cells obtained from the patient before Tr1 treatment.

In one embodiment of the invention, the method of the invention is for assessing whether a patient having a multiple disease and subjected to MBP or MOG-specific Tr1 cell therapy is responding to the treatment.

According to the invention, the above described method is for assessing whether a patient having an arthritic condition and subjected to a Tr1 cell therapy is responding to the treatment. In said treatment, the patient is subjected to a Tr1 cell therapy, wherein the Tr1 cells are specific of a joint-associated antigen.

The term "joint-associated antigen" refers to citrulline-substituted cyclic and linear filaggrin peptides, collagen type II peptides, human cartilage glycoprotein 39 (HCgp39) peptides, HSP, heterogenous nuclear ribonucleoprotein (hnRNP) A2 peptides, hnRNP B1, hnRNP D, Ro60/52, HSP60, 65, 70 and 90, BiP, keratin, vimentin, fibrinogen, collagen type I, III, IV and V peptides, annexin V, Glucose 6 phosphate isomerase (GPI), acetyl-calpastatin, pyruvate deshydrogenase (PDH), aldolase, topoisomerase I, snRNP, PARP, Scl-70, Scl-100, phospholipid antigen including anionic cardiolipin and phosphatidylserine, neutrally charged phosphatidylethanolamine and phosphatidylcholine, matrix metalloproteinase, fibrillin, aggreccan, fragments, variants and mixtures thereof.

The term "arthritic condition" refers to rheumatoid arthritis, polychondritis, septic arthritis, spondyloarthropathies or ankylosing spondylitis, juvenile idiopathic arthritis (JIA), psoriatic arthritis and diseases associated with arthritis such as systemic lupus erythematous, Sjogren's syndrome, scleroderma, dermatomyositis, polymyositis, polymyalgia rheumatica, fibromyalgia, sarcoidosis, or vasculitis.

According to the invention, the cell sample containing T cells obtained from the patient is cultured in the presence of the joint-associated antigen to which the Tr1 cells infused in the patient are directed. After 2 to 10 days, the proliferation of the T cells is assessed and compared to the proliferation of the standard reference, for example the proliferation of T cells obtained from the patient before Tr1 treatment.

In one embodiment of the invention, the method of the invention is for assessing whether a patient having a rheumatoid arthritis and subjected to a type II collagen-specific Tr1 cell therapy is responding to the treatment.

According to the invention, the above described method is for assessing whether a patient having an inflammatory autoimmune condition and subjected to a Tr1 cell therapy is responding to the treatment. In said treatment, the patient is subjected to a Tr1 cell therapy, wherein the Tr1 cells are specific of a human HSP antigen.

The term "human HSP antigen" refers to human HSP60, HSP70, HSP90, fragments, variants and mixtures thereof.

The term "inflammatory autoimmune condition" refers to intestinal inflammatory condition such as Crohn's disease and ulcerative colitis; arthritis condition such as rheumatoid arthritis, psoriatic arthritis, ankylosing spondylitis and juvenile idiopathic arthritis; multiple sclerosis; Wegener's disease; primary biliary cirrhosis; primary sclerosing cholangitis; asthma, transplant rejection (host versus graft disease); or graft versus host disease. More preferably, said inflammatory autoimmune disease is selected in the group of rheumatoid arthritis, Crohn's disease, multiple sclerosis, ulcerative colitis, asthma and transplant rejection or graft versus host disease.

According to the invention, the cell sample containing T cells obtained from the patient is cultured in the presence of the human HSP antigen to which the Tr1 cells infused in the patient are directed. After 2 to 10 days, the proliferation of the T cells is assessed and compared to the proliferation of the standard reference, for example the proliferation of T cells obtained from the patient before Tr1 treatment.

In one embodiment of the invention, the method of the invention is for assessing whether a patient having a rheumatoid arthritis and subjected to a HSP-specific Tr1 cell therapy is responding to the treatment.

According to the invention, the above described method is for assessing whether a patient having an allergic or asthmatic condition and subjected to a Tr1 cell therapy is responding to the treatment. In said treatment, the patient is subjected to a Tr1 cell therapy, wherein the Tr1 cells are specific of an allergen associated with said allergic or asthmatic condition.

Said allergen may be an inhaled allergen, an ingested allergen or a contact allergen. The term "allergic or asthmatic condition" refers to asthma, atopic dermatitis, allergic rhinitis, conjunctivitis, eczema and anaphylaxis.

According to the invention, the cell sample containing T cells obtained from the patient is cultured in the presence of the allergen to which the Tr1 cells infused in the patient are directed. After 2 to 10 days, the proliferation of the T cells is assessed and compared to the proliferation of the standard reference, for example the proliferation of T cells obtained from the patient before Tr1 treatment.

EXAMPLES

Experimental Procedures

Ovalbumin Specific Tr1 Clone Production

Ovalbumin specific Tr1 clones were produced from Peripheral Blood Mononuclear Cells (PBMC) of Crohn's Disease patients. After PBMC isolation by Ficoll gradient density centrifugation (GE Healthcare, Uppsala, Sweden), cells were cultured in the presence of native irradiated ovalbumin (Sigma Aldrich, St-Louis, Mo., USA) in X-Vivo15 (Cambrex, East Rutherford, N.J.) and cytokine-enriched Drosophila feeder cell supernatants at 37° C., 5% CO2. After several days of culture, cells are cloned by limiting dilution method on layers of Drosophila feeder cells in X-Vivo15 at 37° C., 5% CO2. Growing clones are then harvested and tested for antigen specificity and Tr1 cell identity before being expanded on Drosophila feeder cells up to 5 billions.

Drosophila Feeder Cells

Drosophila feeder cells were engineered by TxCell in order to improve the stimulation and growth of Tr1 cell clones. Schneider 2 Drosophila cells were transfected with a transmembrane form of a murine anti-human CD3 antibody, with human CD80, human CD58, human IL-2 and human IL-4. Cells are grown routinely in Express five medium from PAA laboratories (Pashing, Austria).

Tr1 Cell Treatment of Crohn's Disease Patients

A phase I/IIa clinical trial to evaluate the tolerability of Tr1 treatment has started in March 2008 in severe refractory Crohn's disease patients. $10^6$ to $10^9$ Autologous ovalbumin specific Tr1 cells were infused intravenously to the patients at a time when the CDAI (Crohn's Disease Activity Index, see below for description) is above 220 confirming an active disease. Patients where then monitored during 12 weeks for their disease activity.

Clinical Response Assessment

The Crohn's Disease Activity Index or CDAI is a research tool used to quantify the disease activity of patients with Crohn's disease. This is of importance in research studies done on medications used to treat Crohn's disease; most major studies on newer medications use the CDAI in order to define response or remission of disease. A score of more than 220 identifies a patient with active pathology; a CDAI lower or equal to 150 identifies a patient in remission of the disease. A diminution of 100 points of CDAI after patient treatment compared to baseline (CDAI taken before treatment) is considered as a response to treatment (Guidelines on the development of new medicinal products for the treatment of Crohn's disease CPMP/EWP/2284/99).

Thus based on CDAI, patients undergoing autologous ovalbumin-specific Tr1 cell treatment can be sorted in two groups: the clinical responders (patients having a drop of at least 100 points of CDAI after treatment compared to before treatment) and clinical non responders (patients that do not show this drop of 100 points of CDAI after compared to before treatment). The CDAI is calculated at week 0 (the week before infusion) and 1, 3, 5, 8 and/or 12 weeks after Tr1 cell infusion.

CDAI Calculator

| Clinical or laboratory variable | Weighting factor |
|---|---|
| Number of liquid or soft stools each day for seven days | X2 |
| Abdominal pain (graded from 0-3 on severity) each day for seven days | X5 |
| General well being, subjectively assessed from 0 (well) to 4 (terrible) each day for seven days | X7 |
| Presence of complications* | X20 |
| Taking Lomitil or opiates for diarrhea | X30 |
| Presence of an abdominal mass (0 as none, 2 as questionable, 5 as definite) | X10 |
| Absolute deviation of Hematocrit from 47% in men and 42% in women | X6 |
| Percentage deviation from standard weight | X1 |

*Complications: arthralgia, uveitis, erythema nodosum, aphthous ulcers, pyoderma gangrenosum, anal fissure, new fistula, abscess (score 1 per item).

Cell Culture and Proliferation Assessment

At week 0 (the week before infusion) and 1, 3, 8 and 12 weeks after Tr1 cell infusion, patient's peripheral blood was collected and PBMCs were isolated by Ficoll gradient Density centrifugation. Cells were then cultured at $10^6$ cells/ml in the presence or absence of ovalbumin (400 ng/ml) in XVivo15 medium during 5 days at 37° C., 5% $CO_2$. After these five days culture, proliferation of the incubated cells was measured using the WST1 Kit from Roche that allows evaluating the number of viable cells per culture well.

Flow Cytometry

Flow cytometry was performed on PBMC obtained from Crohn's Disease patients before and after treatment with ovalbumin specific Tr1 cells. Cells were stained with fluorescent PerCP-Cy5.5 anti-CD4 monoclonal antibody (clone DK3 from Becton Dickinson Biosciences) and fluorescent APC-labeled anti-FoxP3 antibody (clone PCH101 from eBioscience). Prior to FoxP3 staining, cells were permeabilized using eBioscience Permeabilization Buffer during 30 minutes.

Results

The clinical trial described here aimed at determining the safety and efficacy of a single intravenous administration of autologous ovalbumin-specific Tr1 cells in Crohn's Disease patients with active disease (CDAI above 220). After inclusion and follow-up of 18 patients during 12 weeks after cell infusion, two groups of patients can be sorted based on their response to treatment shown by the CDAI variation compared before and after cell injection (See table 1).

TABLE 1

| Patient number | CDAI before treatment | Lowest CDAI during follow-up | CDAI drop | Response group R = clinical responder NR = clinical Non responder |
|---|---|---|---|---|
| 02 | 305 | 98 | 207 | R |
| 03 | 346 | 52 | 294 | R |
| 04 | 304 | 168 | 136 | R |
| 05 | 384 | 218 | 166 | R |
| 07 | 431 | 211 | 220 | R |
| 08 | 435 | 283 | 152 | R |
| 09 | 530 | 449 | 81 | NR |
| 12 | 277 | 224 | 53 | NR |
| 14 | 363 | 247 | 116 | R |
| 15 | 481 | 416 | 65 | NR |
| 16 | 335 | 230 | 105 | R |
| 17 | 347 | 254 | 93 | NR |
| 19 | 377 | 178 | 199 | R |
| 24 | 212 | 309 | 97 | NR |
| 25 | 396 | 312 | 84 | NR |
| 26 | 360 | 272 | 88 | NR |
| 33 | 292 | 205 | 87 | NR |
| 90 | 485 | 274 | 211 | R |

2 additional patients were included and CDAI data were updated at the end of the clinical trial after control by clinical research associates according to conventional procedure. Results are presented in Table 2. According to Guidelines on the development of new medicinal products for the treatment of Crohn's disease CPMP/EWP/2284/99, the lowest CDAI determined between week 4 and week 8 after Tr1 cells administration were taken into account.

TABLE 2

| Patient number | CDAI before treatment | Lowest CDAI at week 5 or week 8 after treatment | CDAI drop | Response group R = clinical responder NR = clinical Non responder |
|---|---|---|---|---|
| 02 | 303 | 98 | 205 | R |
| 03 | 347 | 51 | 296 | R |
| 04 | 304 | 167 | 137 | R |
| 05 | 383 | 261 | 122 | R |
| 07 | 430 | 220 | 210 | R |
| 08 | 439 | 289 | 150 | R |
| 09 | 528 | 535 | 0 | NR |
| 12 | 277 | 307 | 0 | NR |
| 14 | 364 | 249 | 115 | R |
| 15 | 478 | 480 | 0 | NR |
| 16 | 333 | 258 | 75 | NR |
| 17 | 349 | 319 | 0 | NR |
| 19 | 375 | 178 | 197 | R |
| 24 | 212 | 190 | 22 | NR |
| 25 | 394 | 319 | 75 | NR |
| 26 | 362 | 367 | 0 | NR |
| 33 | 292 | 299 | 0 | NR |
| 90 | 502 | 366 | 136 | R |
| 35 | 293 | 247 | 46 | NR |
| 36 | 308 | 124 | 184 | R |

Results demonstrate that after infusion of autologous ovalbumin specific Tr1 cells, 10 patients show a response to treatment, said response being observed by a drop of the CDAI of at least 100 points after treatment compared to before treatment.

We then compared the ovalbumin specific PBMC proliferation between responder and non-responder groups of patients. For this purpose, PBMC isolated from blood samples collected before or after treatment were cultured in the presence or absence of ovalbumin and the proliferation of the PBMC was evaluated after 5 days of culture.

Figure 1:
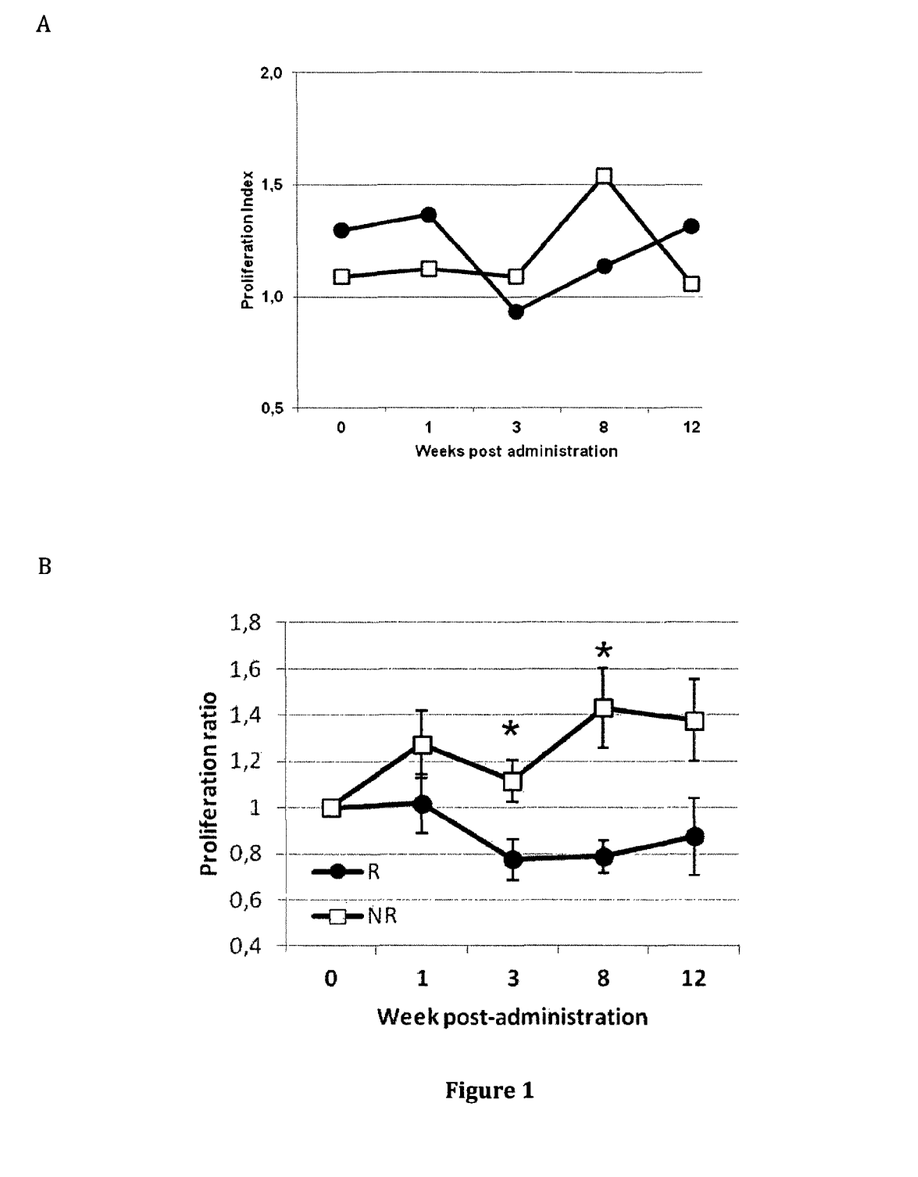
FIG. 1: (A) Kinetic of ovalbumin-specific proliferation of PBMC after treatment with ovalbumin specific Tr1 cells in clinical responder (black circles, n=9) and clinical non-responder Crohn's Disease patients (white squares, n=9). The results are expressed as a mean index of proliferation. (B) Kinetic of ovalbumin-specific proliferation of PBMC after treatment with ovalbumin specific Tr1 cells in clinical responder (black circles, n=10) and clinical non-responder Crohn's Disease patients (black squares, n=10). The results are expressed as a mean ratio of proliferation.

FIG. 1A shows the proliferation index of the two groups during the whole follow-up period. FIG. 1B shows the proliferation ratio of the two groups during the whole follow-up period.

These data show that after treatment, the proliferative response to ovalbumin decreases only in clinical responder patients and not in clinical non-responder patients.

Figure 2:
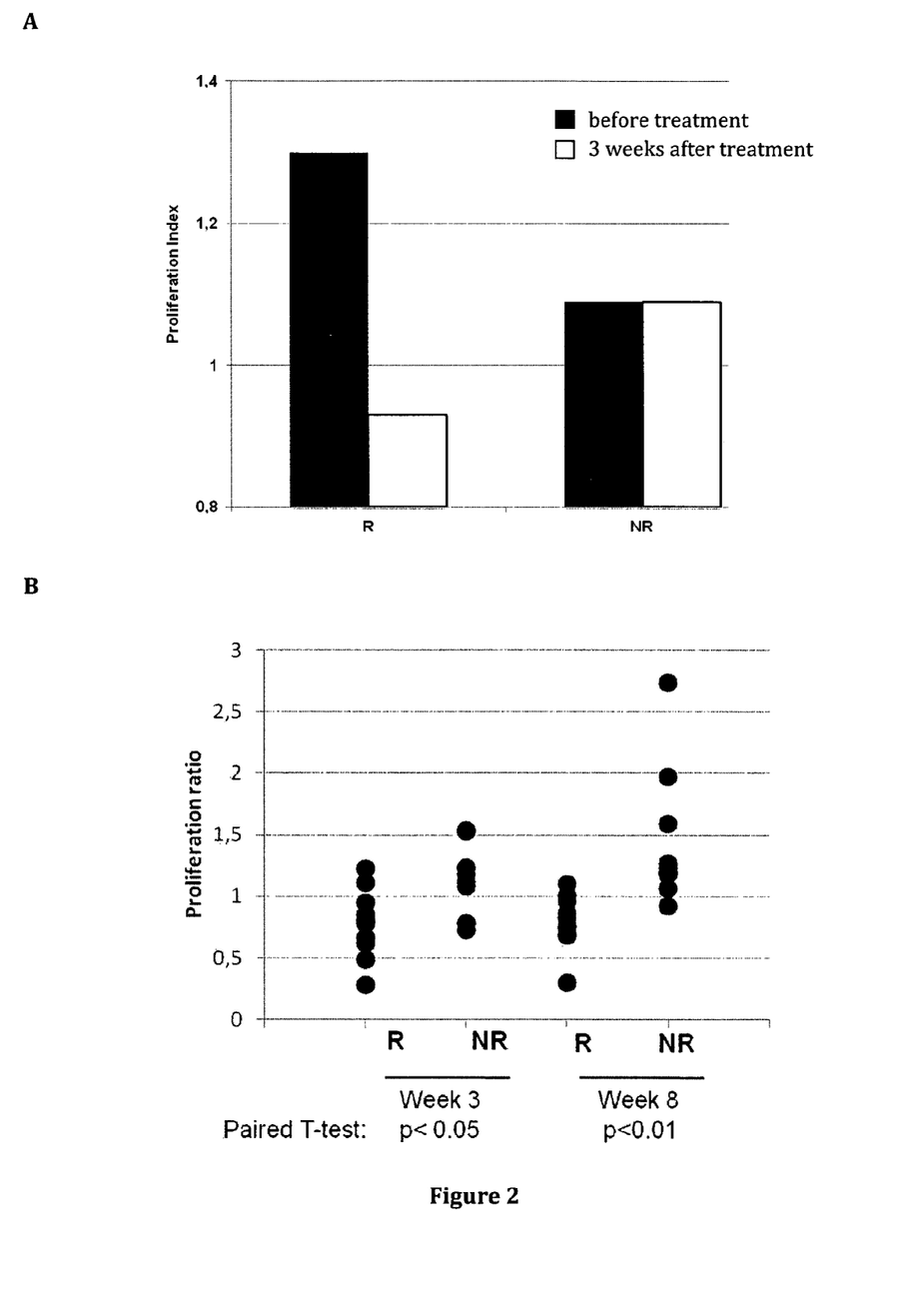
FIG. 2: (A) Kinetic of ovalbumin-specific proliferation of PBMC in clinical responder (CR) and clinical non-responder Crohn's Disease patients (CNR) before ovalbumin specific Tr1 cell treatment (black bars) or 3 weeks (white bars) after ovalbumin specific Tr1 cell treatment. The results are expressed as an index of proliferation. (B) Kinetic of ovalbumin-specific proliferation of PBMC in clinical responder (CR) (n=10) and clinical non-responder Crohn's Disease patients (CNR) (n=10) 3 weeks and 8 weeks after ovalbumin specific Tr1 cell treatment. The results are expressed as a ratio of proliferation.

FIG. 2A shows that specifically at week 3 after Tr1 cell infusion, the proliferative response is decreased in responder patients compared to the proliferative response before Tr1 cell infusion. This suggest that after ovalbumin specific Tr1 cell intravenous infusion, an inhibitory action on the T-cell response to ovalbumin occurs in vivo in the patients that is mediated by the injected cells. This biological response is seen in the majority (60%) of clinical responder patients but in only one patient of the clinical non-responder group (13%) (FIG. 3A).

FIG. 2B shows the proliferative ratio for each responder and non-responder at week 3 and week 8 after Tr1 cell treatment. The mean of proliferative ratios in the responder patients is clearly less than 1 at week 3 and 8 after Tr1 cell treatment, whereas the mean of proliferative ratios in the non-responder patients is clearly more than 1 at week 3 and 8 after Tr1 cell treatment.

Figure 3:
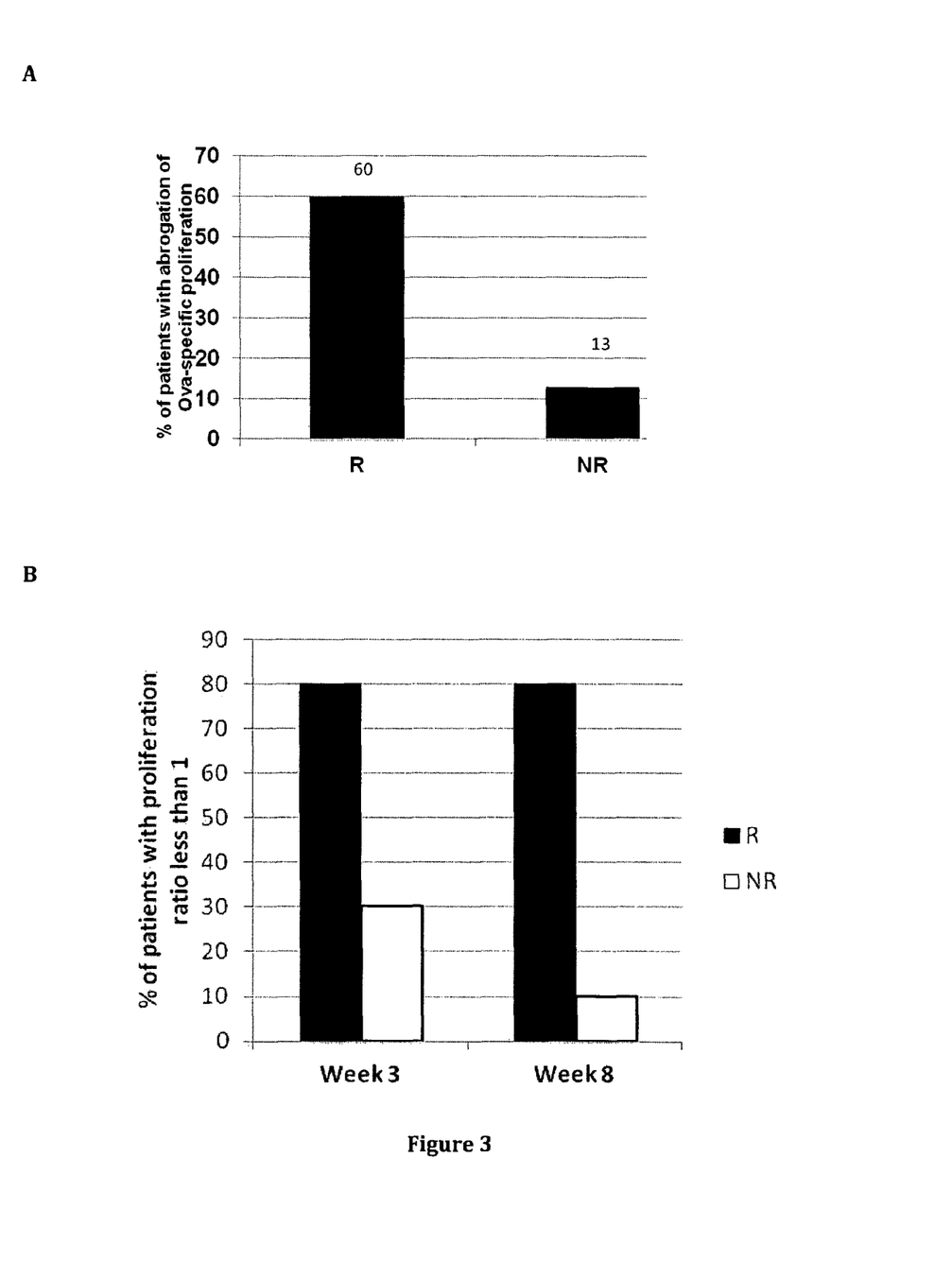
FIG. 3: (A) Percentage of clinical responder (CR) and clinical non-responder Crohn's Disease patients (CNR) showing the abrogation of ovalbumin specific proliferation in vitro 3 weeks after ovalbumin specific Tr1 cell treatment. (B) Percentage of clinical responder (CR) (n=10) and clinical non-responder Crohn's Disease patients (CNR) (n=10) showing a decrease in the ovalbumin specific proliferation in vitro 3 weeks and 8 weeks after ovalbumin specific Tr1 cell treatment.

FIG. 3B shows that a proliferation ratio lower than 1 at week 3 and week 8 is observed in 80% of the responders.

Figure 4:
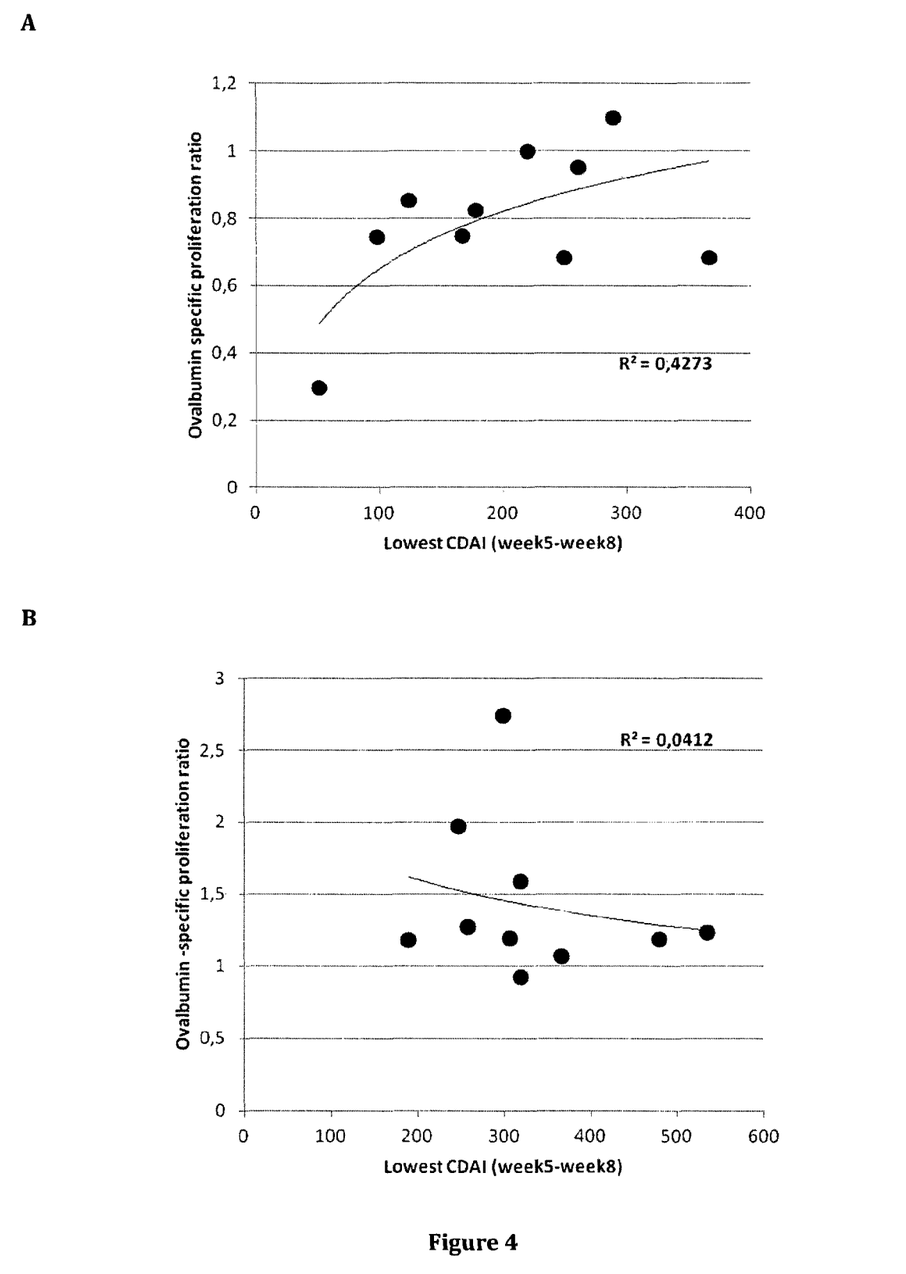
FIG. 4: Plot of ovalbumin-specific proliferation of PBMC from responder patients (Panel A) and non-responder patients (Panel B) in function of the lowest CDAI taken determined between 5 and 8 weeks after ovalbumin specific Tr1 cell treatment. A logarithmic correlation was observed between the ovalbumin-specific proliferation of PBMC from responder patients.

FIG. 4 shows that a proliferation ratio less than 1 is statistically correlated to a diminution of the CDAI at week 5 and week 8 after Tr1 cell treatment in responder patients.

Figure 5:
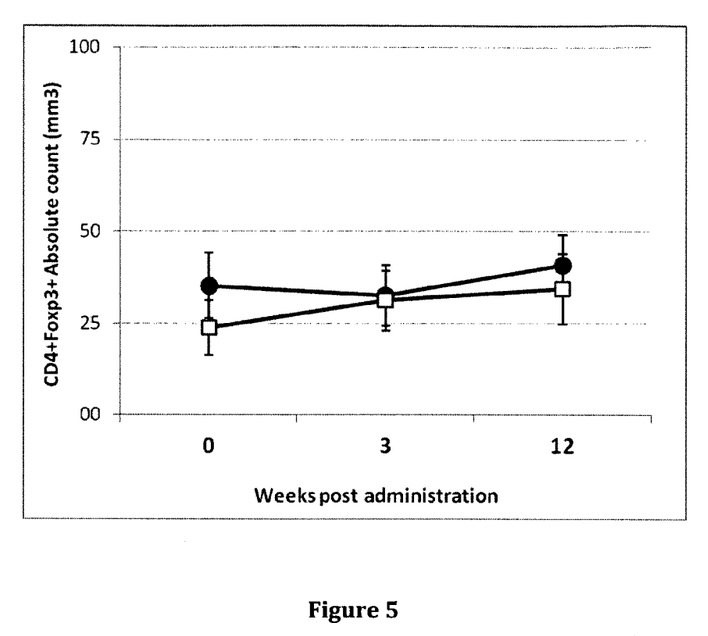
FIG. 5: Evolution of the number of CD4+Foxp3+ T cells in the blood of responder (black circles) and non-responder Crohn's Disease patients (white circles) measured by Flow cytometry. Results are expressed as the number of CD4+Foxp3+(absolute counts) (mm3). Error bars are s.e.m.

FIG. 5 shows that the number of activated regulatory T cells (CD4+ Foxp3+ cells) in the blood of responder or non-responder patients is similar. Moreover, the number of activated regulatory T cells in the blood of responder or non-responder patients does not fluctuate after Tr1 cell therapy. Indeed, there is no difference between the number of regulatory T cells in the blood of patients at week 0, at week 3 and at week 12 after Tr1 cell infusion.

This result shows that the decrease in the proliferative response to ovalbumin in responder patients is not due to an increase in the total number of regulatory T cells in the blood of these patients.

The invention claimed is:

1. A method for assessing whether a human patient subjected to an antigen-specific Tr1 cell therapy is responding to the treatment, said method comprising:
   determining in vitro the antigen-specific proliferation of T cells contained in a cell sample from said patient,
   comparing said antigen-specific proliferation to a standard reference,
   thereby determining whether the patient is responding or not responding to the treatment.

2. The method according to claim 1, wherein the standard reference is the antigen-specific proliferation of T cells contained in a cell sample obtained from said patient before said Tr1 cell therapy.

3. The method according to claim 1, wherein the in vitro determination of the antigen specific proliferation of T cells is carried out in a cell sample obtained from the patient between day 5 and day 30 after the last administration of Tr1 cells to the patient.

4. The method according to claim 1, wherein the cell sample is peripheral blood mononuclear cells or peripheral white blood cells, or is obtained from a lymph nodes biopsy, an intestinal biopsy, a synovial biopsy, a cerebrospinal fluid or from a bronchoalveolar lavage.

5. The method according to claim 1, wherein determining the antigen-specific proliferation of T cells comprises:
   culturing the cell sample containing T cells in the presence of the antigen to which the Tr1 cells are directed, and
   determining the proliferation of T cells after 2 to 10 days of culture.

6. The method according to claim 1, wherein the method is repeated each week on a cell sample obtained from the patient each week during day 5 to day 30.

7. The method according to claim 1, wherein the method is repeated every two weeks on a cell sample obtained from the patient every two weeks during day 5 to day 30.

8. The method according to claim 1, further comprising sorting the patient into a responder group or non-responder group.

9. A method for assessing whether a human patient suffering from a disease and subjected to an antigen-specific Tr1 cell therapy for the disease is responding to the treatment, said method comprising:
   determining in vitro the antigen-specific proliferation of T cells contained in a cell sample from said patient,
   comparing said antigen-specific proliferation to a standard reference,
   thereby determining whether the patient is responding or not responding to the treatment.

10. The method according to claim 9, wherein the disease is Crohn's disease and the treatment is an ovalbumin-specific Tr1 cell therapy.

11. The method according to claim 9, wherein the disease is rheumatoid arthritis and the treatment is a type II collagen-specific Tr1 cell therapy.

* * * * *